United States Patent [19]

Peppard

[11] Patent Number: 5,166,488
[45] Date of Patent: Nov. 24, 1992

[54] HYPODERMIC SYRINGE AND NEEDLE DISPOSAL

[76] Inventor: Dennis L. Peppard, 580 Seminoe, Casper, Wyo. 82609

[21] Appl. No.: 693,322

[22] Filed: Apr. 29, 1991

[51] Int. Cl.$^5$ .............................................. H05B 6/64
[52] U.S. Cl. ...................... 219/10.55 R; 219/10.55 F; 219/10.55 A; 219/68; 241/65; 423/DIG. 20
[58] Field of Search ............... 219/10.55 A, 10.55 F, 219/10.55 E, 10.55 R, 68; 100/90, 92; 264/0.5, 1.4; 83/944; 241/99, 100, 235, 259, DIG. 38, DIG. 31, 65; 206/365, 366, 367, 370, 373; 423/DIG. 20

[56] References Cited

U.S. PATENT DOCUMENTS

| | | | |
|---|---|---|---|
| 3,589,276 | 6/1971 | Swallert | 241/259 |
| 3,701,872 | 10/1972 | Levinson | 219/10.55 R |
| 3,750,966 | 8/1973 | Anderson | 241/235 |
| 4,330,946 | 5/1982 | Courneya | 219/10.55 R |
| 4,485,918 | 12/1984 | Mayer | 206/366 |
| 4,539,453 | 9/1985 | Ishino et al. | 219/10.55 D |
| 4,545,540 | 10/1985 | Nakamura | 241/99 |
| 4,860,958 | 3/1989 | Yerman | 241/99 |
| 4,965,426 | 10/1990 | Colombo | 219/68 |
| 4,984,748 | 1/1991 | Kimura | 241/100 |
| 5,005,496 | 4/1991 | Nagata | 110/346 |
| 5,091,621 | 2/1992 | Butler | 219/68 |

Primary Examiner—Bruce A. Reynolds
Assistant Examiner—Tuan V. To
Attorney, Agent, or Firm—Dean P. Edmundson

[57] ABSTRACT

Apparatus is disclosed for safely and simply disposing of hypodermic syringes and needles. The apparatus includes: (a) a housing or enclosure; (b) microwave generator, (c) microwave absorber, and (d) a syringe receiver heated by the microwave absorber to a temperature greater than the melting point of the needle. The apparatus is self-contained and can be provided in any desired size.

13 Claims, 6 Drawing Sheets

HYPODERMIC SYRINGE AND NEEDLE DISPOSAL

FIELD OF THE INVENTION

This invention relates to methods, techniques and apparatus for disposal of hypodermic syringes and needles. More particularly, this invention relates to improved techniques for safely disposing of hypodermic needles and syringes to prevent contamination and spread of disease.

BACKGROUND OF THE INVENTION

Throughout the health care profession there is the danger of needle-sticks when handling used or contaminated syringes and needles. In addition to the danger of HIV infection, which leads to AIDS, there is the danger of being contaminated with the multitude of other infectious diseases, including for example Hepatitis B. These dangers add to the daily concern of health care workers, as well as other people involved with these devices from initial use to eventual destruction and disposal of the devices, for their own health and safety. This includes, for example, nurses, doctors, janitorial personnel, medical waste disposal personnel, loading dock workers, incinerator operators and landfill workers.

Sometimes contaminated syringes and needles are simply discarded in conventional trash containers. This is extremely dangerous and can easily lead to needle-sticks when the trash containers are handled or emptied. A more approved disposal method includes placing the syringes and needles in sharps containers which then must be re-packaged, sealed and marked prior to pick-up for delivery to an approved medical waste disposal facility for proper destruction. This procedure involves much time, effort, paperwork and expense. Additionally, there is still the danger of injury or infection to personnel due to the multiple handlings of used syringes and needles.

It is an object of this invention to provide improved techniques and apparatus for safely disposing of contaminated syringes and needles.

It is another object of this invention to reduce the time, effort, paperwork and economic cost which is associated with the disposition of used or contaminated needles and syringes.

It is still another object of this invention to significantly reduce the risk of injury or infection to health care professionals and all other personnel who handle used or contaminated syringes and needles.

SUMMARY OF THE PRESENT INVENTION

In accordance with the present invention there is provided a technique and apparatus for safely and effectively disposing of used hypodermic syringes. In a preferred embodiment the apparatus comprises:
 (a) a housing;
 (b) microwave generating means within the housing;
 (c) microwave absorbing means for absorbing microwaves generated by the generating means; and
 (d) syringe receiving means in the housing.

The syringe receiving means is heated by the microwave absorbing means to a temperature greater than the melting point of the metal needle in the syringe. The plastic portions of the syringe melt and are decomposed and converted into gaseous vapors which are preferably drawn away by means of vacuum and then passed into a filter which removes the toxic vapors and permits air to pass through.

The melted metal from the needle drops downwardly into a collector pan or trough where it is permitted to cool and harden. When the collector is full, the metal can be simply removed and discarded or recycled in conventional manner.

The apparatus and techniques of this invention provide for very safe and effective disposal of used or contaminated syringes and needles. This avoids the risks to the persons who would otherwise have to handle such devices.

The apparatus of the invention can be provided in any desired size. It can be used in clinics, doctor's offices, infirmaries, hospitals, etc. or wherever syringes and needles are used for injections, drawing blood, etc.

Due to the increased awareness and a multitude of new regulations governing the handling, destruction and disposal of medical waste and needles/syringes in particular, the apparatus of this invention offers the safety, efficiency, and cost effectiveness now enjoyed by large medical waste incinerators to individual doctor's offices and clinics. Use of this apparatus also significantly reduces the risk of injury and infection to hundreds of thousands of personnel associated with the health care field by eliminating the problem at the source and by avoiding multiple handling risks.

Other advantages of the apparatus and techniques of the present invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
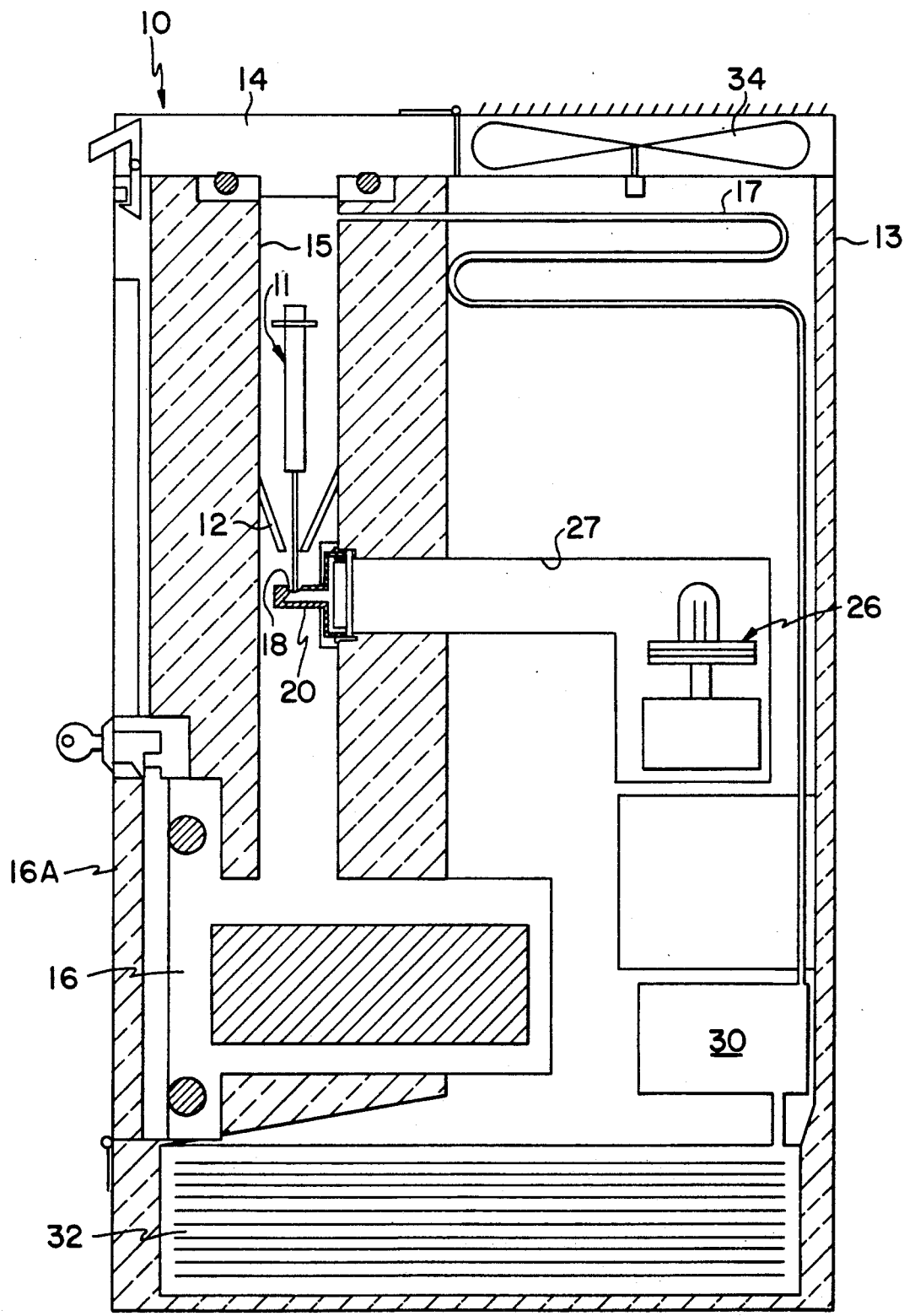
FIG. 1 is a side elevational cut-away view illustrating a preferred embodiment of apparatus of the invention.
Figure 2:
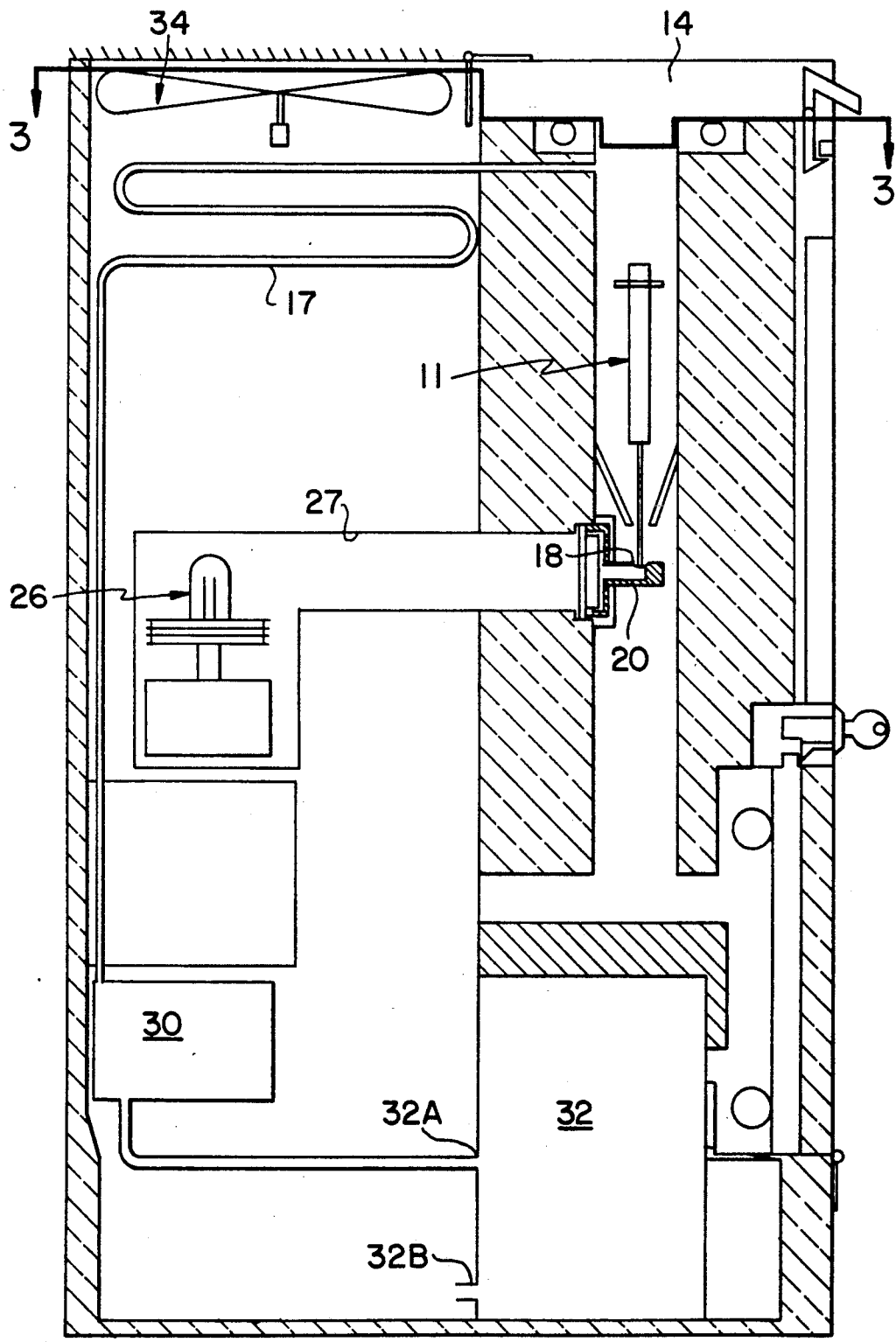
FIG. 2 is a side elevational cut-away view of the apparatus of FIG. 1 from the opposite side as shown in FIG. 1.
Figure 3:
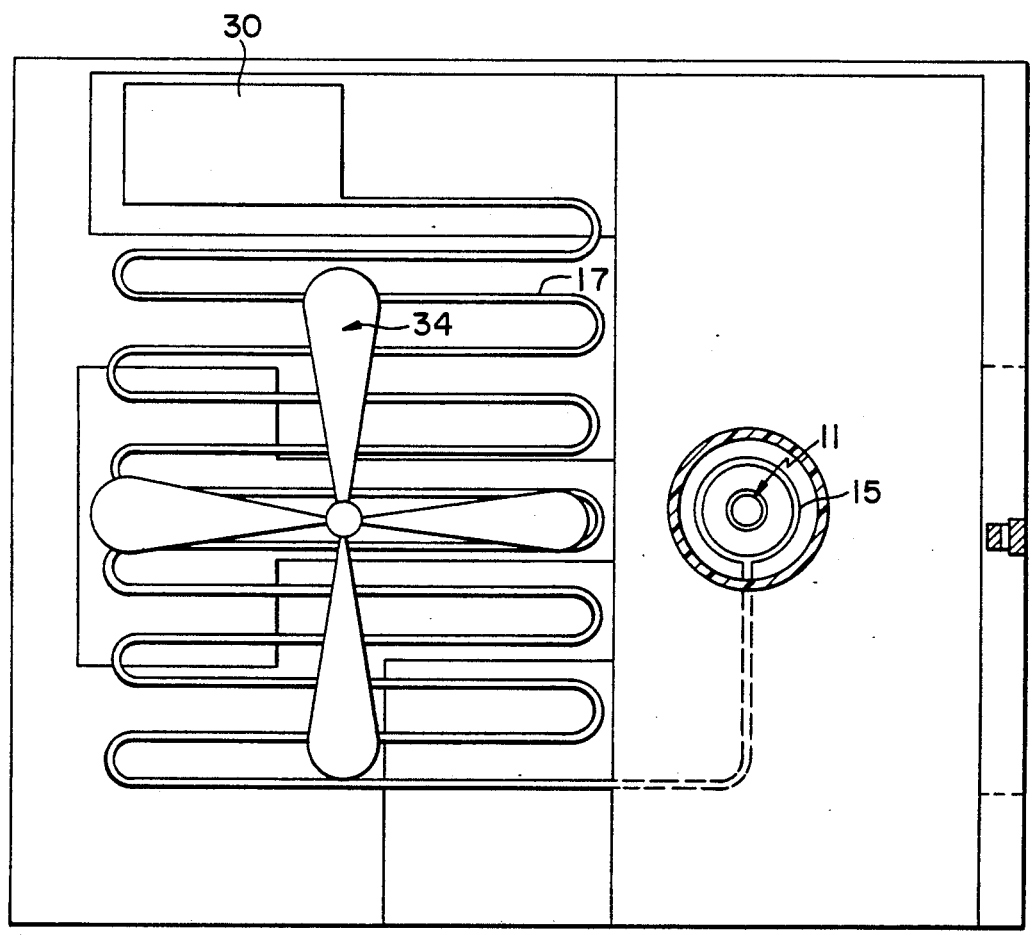
FIG. 3 is a top cut-away view of the apparatus taken along line 3—3 in FIG. 2.
Figure 4:
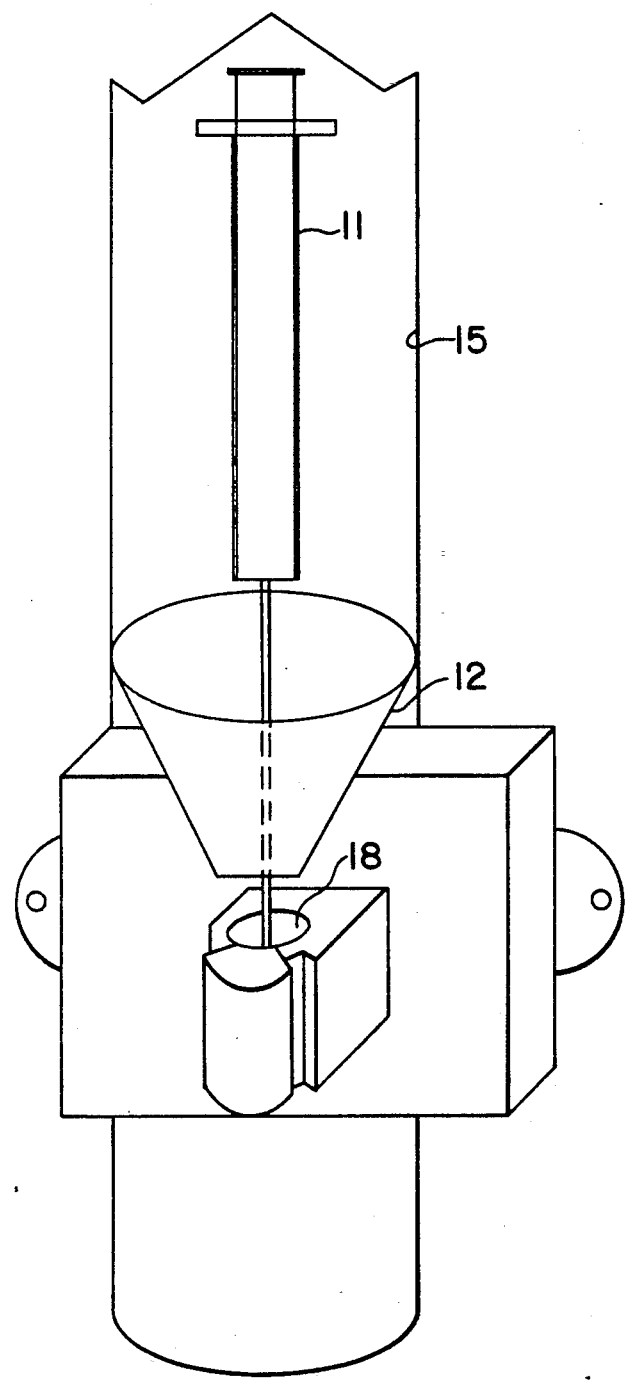
FIG. 4 is an isometric view showing the manner in which the syringe is received in a heated melted cavity or crucible.
Figure 5:
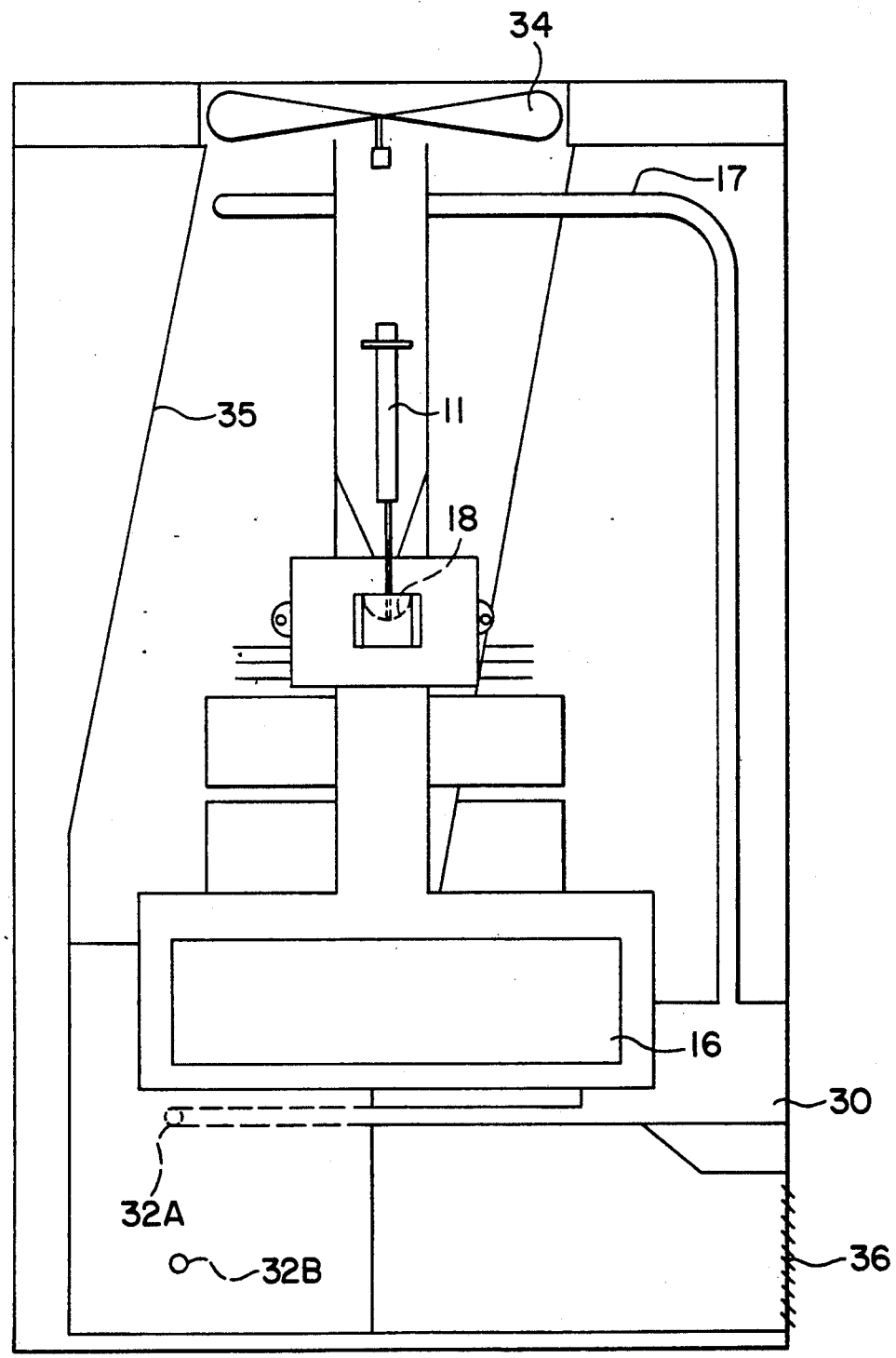
FIG. 5 is a front elevational cut-away view of the apparatus of FIG. 1.

In the drawings there is shown a preferred embodiment of apparatus 10 for safely and effectively disposing of a hypodermic syringe 11 of the type including a needle (e.g., a metal needle) and a plastic barrel. The apparatus includes a housing 13 having a hinged door 14 on its upper surface. A vertical tubular body or receiver 15 extends from the upper portion of the apparatus (adjacent the hinged door) to the lower portion of the apparatus where there is a collector pan or trough 16 (accessible through hinged door 16A).

Within the tubular receiver 15 there is disposed a crucible 18 or other such heated melting pot or recess which is supported by, or is adjacent to, microwave absorbing means 20. A funnel 12 serves to guide the syringe to the crucible 18. The funnel is preferably ceramic and is preferably heated to at least about 250° F. (e.g., by means of an electrical resistance heater) so that the plastic portions of a syringe will melt and flow down the funnel into the heated crucible.

A microwave generator 26 is contained within the housing and is surrounded by suitable insulation. Microwaves which are generated here are guided by guide tube 27 to one end of microwave absorbing means 20. The microwave generator is conventional and is commercially available. For example, it may be obtained from Panasonic as Model 2M210-M1Z. Microwave generators are also available from Amana.

Larger or higher wattage microwave generators can also be used, if desired. For example, a Klystron amplifier Model VKS 8269A is available from Varian. By increasing the wattage of the microwave generator it is possible to reduce the number of generators required to heat a given volume of material.

Electrical energy to power the apparatus of the invention may be supplied by a generator or by conventional electrical source. A transformer converts the electrical energy to high voltage AC current which is then sent to a half wave doubler circuit to produce high voltage D.C. current. The doubler circuit may be comprised of a single diode and one capacitor, for example. The DC current is supplied to the microwave generator to produce microwave.

The microwave absorbing means 20 preferably comprises carbon. As it absorbs the microwave produced by the generator 26, the carbon becomes heated to a higher temperature. The heat is conducted through the carbon to the recess area or crucible 18 which then also becomes heated (e.g., to a temperature of at least about 2,700° F.) The crucible is preferably composed of alumina and includes an opening in the recessed area such that the heated carbon in the recessed area is exposed. If desired, the carbon adjacent the opening can be coated with a heat-conductive material.

The recessed area becomes heated to a temperature greater than the melting point of the metal needle. As a result, the needle melts in the crucible. When the crucible overflows with molten metal, the metal drops downwardly into the collector 16 where it cools and hardens. When the collector becomes full, the hardened metal can be removed and recycled in conventional manner, if desired.

The plastic portions of the syringe are vaporized by the high temperature of the crucible. The vapors are drawn off of tubular receiver 15 through conduit 17 by virtue of vacuum pump 30. The vapors are passed through a conventional filter unit 32 to remove any vapors which are toxic or offensive. Air enters the filter through inlet 32A and exits through outlet 32B.

The filter unit 32 which may be used is commercially available, for example, from North Safety Equipment, as the N7500 Series. Other conventional filters may also be suitable for removing toxic or offensive fumes from the air. Alternatively, the fumes could be passed through a conventional liquid scrubber, or the fumes could be vented outside of the building in which the apparatus is located.

Fan 34 at the top of the housing pushes cooling air downwardly over conduit 17 so as to cool the conduit. Ductwork 35 guides the air through the housing from the inlet area at the top to an outlet 36 at the bottom.

Figure 6:
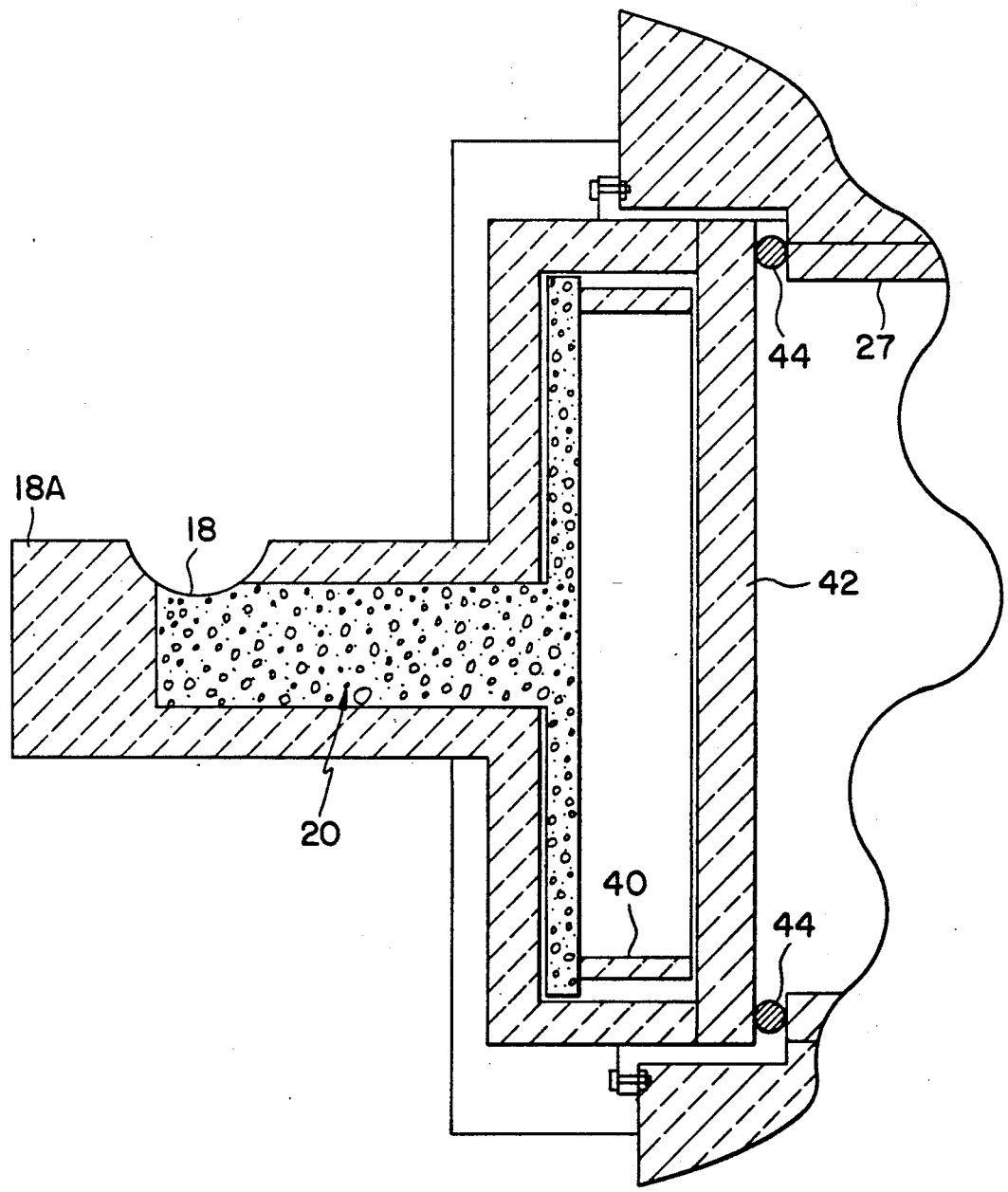
FIG. 6 is a cross-sectional view of the heating element and melting cavity.

FIG. 6 illustrates a preferred embodiment of microwave absorbing means and the means for heating and melting a needle being disposed. The microwave absorbing means 20 comprises carbon which is positioned within crucible 18A. A refractory ring 40 (e.g., fused silica) and glass plate 42 serve to hold the carbon in place within the crucible during use. O-ring 44 forms a seal between the glass plate and the insulation surrounding the guide tube 27.

As shown in FIG. 6, the crucible 18A includes a recessed area 18 which is open at the bottom, whereby the heated carbon 20 is exposed at the bottom of the recessed area to heat and melt the needles which are being disposed. If desired, the carbon surface at the opening in the recessed area may be coated with a ceramic material. The crucible is preferably alumina and has a melting point greater than about 3000° F.

The apparatus of the invention is very effective and convenient for disposing of used or contaminated hypodermic syringes and needles. The apparatus, for example, may be used in doctors' offices, clinics, infirmaries, hospitals, etc. The apparatus may include more than one tubular receiver and heated crucible or melting pot, if desired.

Other variants are possible without departing from the scope of this invention.

What is claimed is:

1. Apparatus for disposing of a hypodermic syringe of the type including a needle, said apparatus comprising:
   (a) a housing;
   (b) microwave generating means within said housing;
   (c) microwave absorbing means for absorbing microwaves generated by said generating means;
   (d) syringe receiving means in said housing adjacent said microwave absorbing means; and
   (e) collector means disposed beneath said syringe receiving means for collecting molten metal produced by a melting of a said needle;
wherein said syringe receiving means is heated by said microwave absorbing means to a temperature greater than a melting point of said needle.

2. Apparatus in accordance with claim 1, wherein said syringe receiving means comprises a crucible supported by said microwave absorbing means.

3. Apparatus in accordance with claim 2, wherein said syringe receiving means further includes a funnel-shaped guide above said crucible, wherein said guide is heated to a temperature of at least about 250° F.

4. Apparatus in accordance with claim 1, wherein said microwave absorbing means comprises carbon.

5. Apparatus in accordance with claim 1, further comprising vacuum means within said housing and adapted to remove vapors from said syringe receiving means.

6. Apparatus in accordance with claim 5, further comprising a filter operatively connected to said vacuum means for filtering said vapors.

7. Apparatus in accordance with claim 5, further comprising (a) tubular conduit extending between said syringe receiving means and said vacuum means, and (b) fan means for drawing air into said housing and past said tubular conduit.

8. Apparatus for disposing of a hypodermic syringe of the type including a needle, said apparatus comprising:
   (a) a housing;
   (b) microwave generating means within said housing;
   (c) microwave absorbing means for absorbing microwaves generated by said generating means;
   (d) syringe receiving means in said housing adjacent said microwave absorbing means;

(e) collector means disposed beneath said syringe receiving means for collecting molten metal produced by the melting of said needle;

(f) vacuum means within said housing for removing vapors from said syringe receiving means;

wherein said syringe receiving means is heated by said microwave absorbing means to a temperature greater than a melting point of said needle.

9. Apparatus in accordance with claim 8, wherein said syringe receiving means comprises a crucible supported by said microwave absorbing means.

10. Apparatus in accordance with claim 9, wherein said syringe receiving means further includes a funnel-shaped guide above said crucible, wherein said guide is heated to a temperature of at least about 250° F.

11. Apparatus in accordance with claim 8, wherein said microwave absorbing means comprises carbon.

12. Apparatus in accordance with claim 9, further comprising a filter operatively connected to said vacuum means for filtering said vapors.

13. Apparatus in accordance with claim 9, further comprising (a) tubular conduit extending between said syringe receiving means and said vacuum means, and (b) fan means for drawing air into said housing and past said tubular conduit.

* * * * *